US009398904B2

United States Patent
Stanley

(10) Patent No.: US 9,398,904 B2
(45) Date of Patent: *Jul. 26, 2016

(54) EXTERNAL SUTURE SECUREMENT DEVICES AND METHODS

(71) Applicant: Cook Medical Technologies LLC, Bloomington, IN (US)

(72) Inventor: Cleon Stanley, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/829,054

(22) Filed: Aug. 18, 2015

(65) Prior Publication Data

US 2015/0351742 A1 Dec. 10, 2015

Related U.S. Application Data

(63) Continuation of application No. 13/764,105, filed on Feb. 11, 2013, now Pat. No. 9,107,655.

(60) Provisional application No. 61/599,677, filed on Feb. 16, 2012.

(51) Int. Cl.
*A61B 17/04* (2006.01)

(52) U.S. Cl.
CPC .......... *A61B 17/0401* (2013.01); *A61B 17/0487* (2013.01); *A61B 2017/0414* (2013.01); *A61B 2017/0417* (2013.01); *A61B 2017/0488* (2013.01)

(58) Field of Classification Search
CPC .......... A61B 17/0401; A61B 17/0487; A61B 2017/0488; A61B 17/04; A61B 2017/0417; A61B 2017/0446; A61B 2017/0456; A61B 2017/0458
USPC .............................. 606/151, 157, 232; 57/1 R
See application file for complete search history.

(56) References Cited

U.S. PATENT DOCUMENTS

| | | | |
|---|---|---|---|
| 1,811,738 A | 6/1931 | Williams | |
| 2,557,877 A | 6/1951 | Kluson | |
| 3,064,648 A | 11/1962 | Bujan | |
| 3,910,281 A | 10/1975 | Kletschka et al. | |
| 4,291,698 A | 9/1981 | Fuchs et al. | |
| 4,705,040 A | 11/1987 | Mueller et al. | |
| 4,750,492 A | 6/1988 | Jacobs | |
| 4,773,421 A | 9/1988 | Davis | |
| 4,890,966 A | 1/1990 | Umezawa | |
| 5,258,015 A | 11/1993 | Li et al. | |
| 5,306,280 A | 4/1994 | Bregen et al. | |

(Continued)

FOREIGN PATENT DOCUMENTS

GB 2066891 7/1981
WO WO 03/077728 A2 9/2003

*Primary Examiner* — Jonathan W Miles
*Assistant Examiner* — George J Ulsh
(74) *Attorney, Agent, or Firm* — Woodard, Emhardt, Moriarty, McNett & Henry LLP

(57) ABSTRACT

Described are devices, methods and systems for securing sutures external to the body. In certain aspects, a suture securement device includes a base paddle defining a slot and a suture aperture in communication with the slot, and a rotating paddle having an extension arm with a suture aperture. In such embodiments, the extension arm can rotate within the slot to frictionally crimp a suture, such that the suture is substantially prevented from moving with the apertures.

35 Claims, 8 Drawing Sheets

(56) References Cited

U.S. PATENT DOCUMENTS

| | | |
|---|---|---|
| 5,342,321 A | 8/1994 | Potter |
| 5,345,657 A | 9/1994 | Shimizu |
| 5,383,905 A | 1/1995 | Golds et al. |
| 5,514,159 A | 5/1996 | Matula et al. |
| 5,531,763 A | 7/1996 | Mastri et al. |
| 5,536,273 A | 7/1996 | Lehrer |
| 5,630,824 A | 5/1997 | Hart |
| 5,651,771 A | 7/1997 | Tangherlini et al. |
| 5,653,711 A | 8/1997 | Hayano et al. |
| 5,666,699 A | 9/1997 | Takahashi |
| 5,681,351 A | 10/1997 | Jamiolkowski et al. |
| 5,693,032 A | 12/1997 | Bierman |
| 5,722,959 A | 3/1998 | Bierman |
| 5,810,853 A | 9/1998 | Yoon |
| 5,919,208 A | 7/1999 | Valenti |
| 6,010,525 A | 1/2000 | Bonutti et al. |
| 6,110,183 A | 8/2000 | Cope |
| 6,126,677 A | 10/2000 | Ganaja et al. |
| 6,200,329 B1 | 3/2001 | Fung et al. |
| 6,491,664 B2 | 12/2002 | Bierman |
| 6,979,320 B2 | 12/2005 | Bierman |
| 7,048,755 B2 | 5/2006 | Bonutti et al. |
| 7,081,126 B2 | 7/2006 | McDevitt et al. |
| 7,090,690 B2 | 8/2006 | Foerster et al. |
| 7,108,710 B2 | 9/2006 | Anderson |
| 7,300,451 B2 | 11/2007 | Crombie et al. |
| 7,326,233 B2 | 2/2008 | Hart et al. |
| 7,416,556 B2 | 8/2008 | Jackson |
| 7,517,357 B2 | 4/2009 | Abrams et al. |
| 7,666,196 B1 | 2/2010 | Miles |
| 7,674,276 B2 | 3/2010 | Stone et al. |
| 7,686,830 B2 | 3/2010 | Collier et al. |
| 7,837,710 B2 | 11/2010 | Lambardo et al. |
| 7,867,253 B2 | 1/2011 | McMichael et al. |
| 7,875,056 B2 | 1/2011 | Jervis et al. |
| 8,007,515 B2 | 8/2011 | Paolitto et al. |
| 8,100,923 B2 | 1/2012 | Paraschact et al. |
| 2004/0102809 A1 | 5/2004 | Anderson |
| 2005/0288711 A1 | 12/2005 | Fallin et al. |
| 2006/0200199 A1 | 9/2006 | Bonutti et al. |
| 2007/0073342 A1 | 3/2007 | Stone et al. |
| 2008/0065157 A1 | 3/2008 | Crombie et al. |
| 2009/0062853 A1 | 3/2009 | McMichael et al. |
| 2010/0063542 A1 | 3/2010 | van der Burg et al. |
| 2010/0121348 A1 | 5/2010 | van der Burg et al. |
| 2012/0046747 A1 | 2/2012 | Justin et al. |

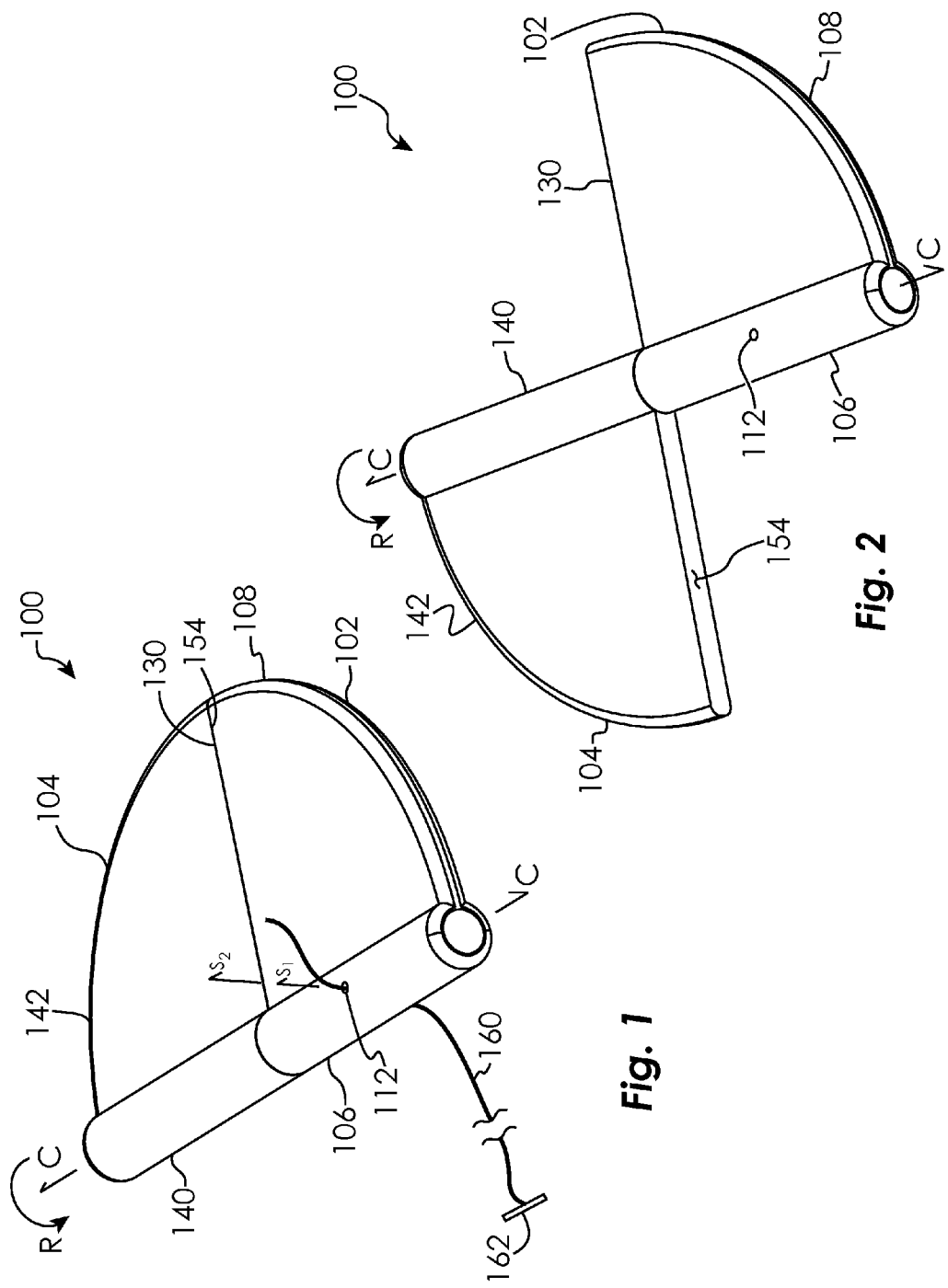

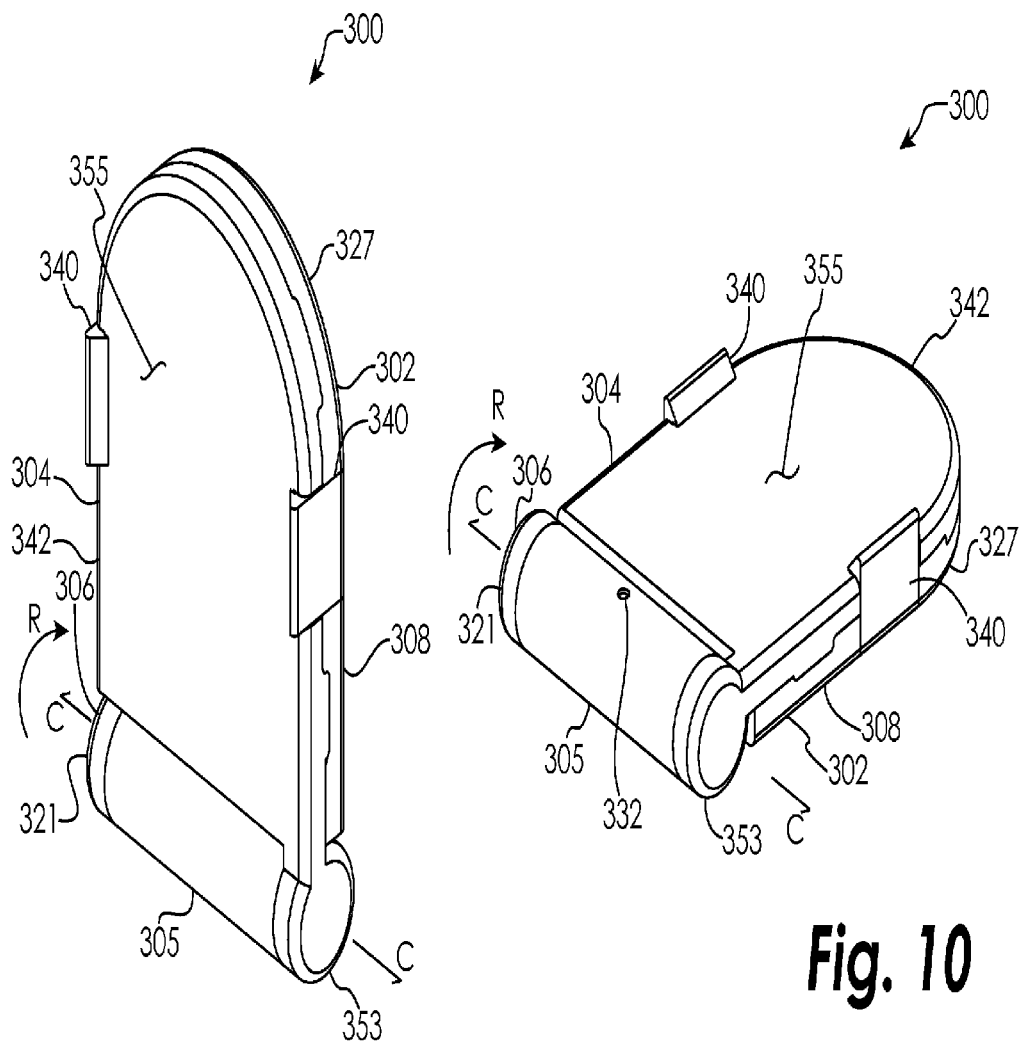

EXTERNAL SUTURE SECUREMENT DEVICES AND METHODS

REFERENCE TO RELATED APPLICATION

This application is a continuation of U.S. patent application Ser. No. 13/764,105, filed Feb. 11, 2013 which claims the benefit of U.S. Provisional Patent Application No. 61/599,677, filed Feb. 16, 2012, which is hereby incorporated by reference.

BACKGROUND

The present disclosure relates generally to medical technology and in particular aspects to devices, methods and systems for securing sutures external to the patient's body. As further background, there exist a variety of medical procedures in which suture and anchor sets are necessary to secure patient tissue before, during and/or after the procedure. In such procedures, it is often necessary to secure the suture material outside of the body to ensure that the corresponding anchor device maintains its position. Many aspects of such procedures often rely, in part, on the successful securement of the suture material outside of the body.

Several methods have been suggested for securing suture material, including various methods of tying the suture or crimping the suture. However, such arrangements can lose integrity over time or upon the application of force along the suture and anchor set. Additionally, such arrangements can be difficult uncomfortable to the patient, and/or create undesirable effects at the point of contact with the patient's skin. Other arrangements which have been suggested for crimping or clamping suture material external to the body are often difficult for the medical personnel to handle and manipulate.

There remain needs for improved and/or alternative systems and methods for securing suture material external to the patient's body. The present disclosure is addressed to those needs.

SUMMARY

The present disclosure provides, in certain aspects, unique methods and systems for securing sutures external to the patient's body for use in medical procedures. In certain embodiments, the present disclosure provides unique methods and systems for securing sutures via crimping sutures along tortuous paths.

In one embodiment, a suture securement system includes a base paddle defining a slot and a rotating paddle with an extension arm configured to be slideably advanced and rotatable within the slot. The rotating paddle and the base paddle each include a suture aperture through which a suture is threaded. The rotation of the rotating paddle operates to crimp the suture to secure it. In the uncrimped configuration, the rotating paddle and the base paddle may optionally cooperate to form a handle.

In another embodiment, a suture securement system includes a base paddle defining a slot and a rotating paddle with an extension arm configured to be slideably advanced and rotatable within the slot. The rotating paddle and the base paddle each include a suture aperture through which a suture is threaded. The rotation of the rotating paddle operates to crimp the suture to secure it. Additionally, the paddles may be clamped and locked together to further assist in securing the suture.

In yet another embodiment, a suture securement system includes a base paddle defining a slot and a rotating paddle with an extension arm configured to be slideably advanced and rotatable within the slot. Additionally, the system includes a center cylindrical sleeve defining a slot through which portions of the paddles are configured to be slideably advanced and rotated. The rotating paddle, the base paddle and the sleeve each include a suture aperture through which a suture is threaded. The rotation of the rotating paddle and optionally the base paddle operates to crimp the suture to secure it. Additionally, the paddles may be clamped and locked together to further assist in securing the suture.

Other objects, embodiments, forms, features, advantages, aspects, and benefits of the present disclosure shall become apparent from the detailed description and drawings included herein.

BRIEF DESCRIPTION OF THE DRAWINGS

FIG. 1 is a perspective view of an inventive medical system according to an embodiment of the present disclosure.

FIG. 2 is another perspective view of the medical system of FIG. 1.

FIG. 9 is yet another perspective view of the medical system of FIG. 7.

FIG. 10 is yet another perspective view of the medical system of FIG. 7.

DETAILED DESCRIPTION

Figure 3:
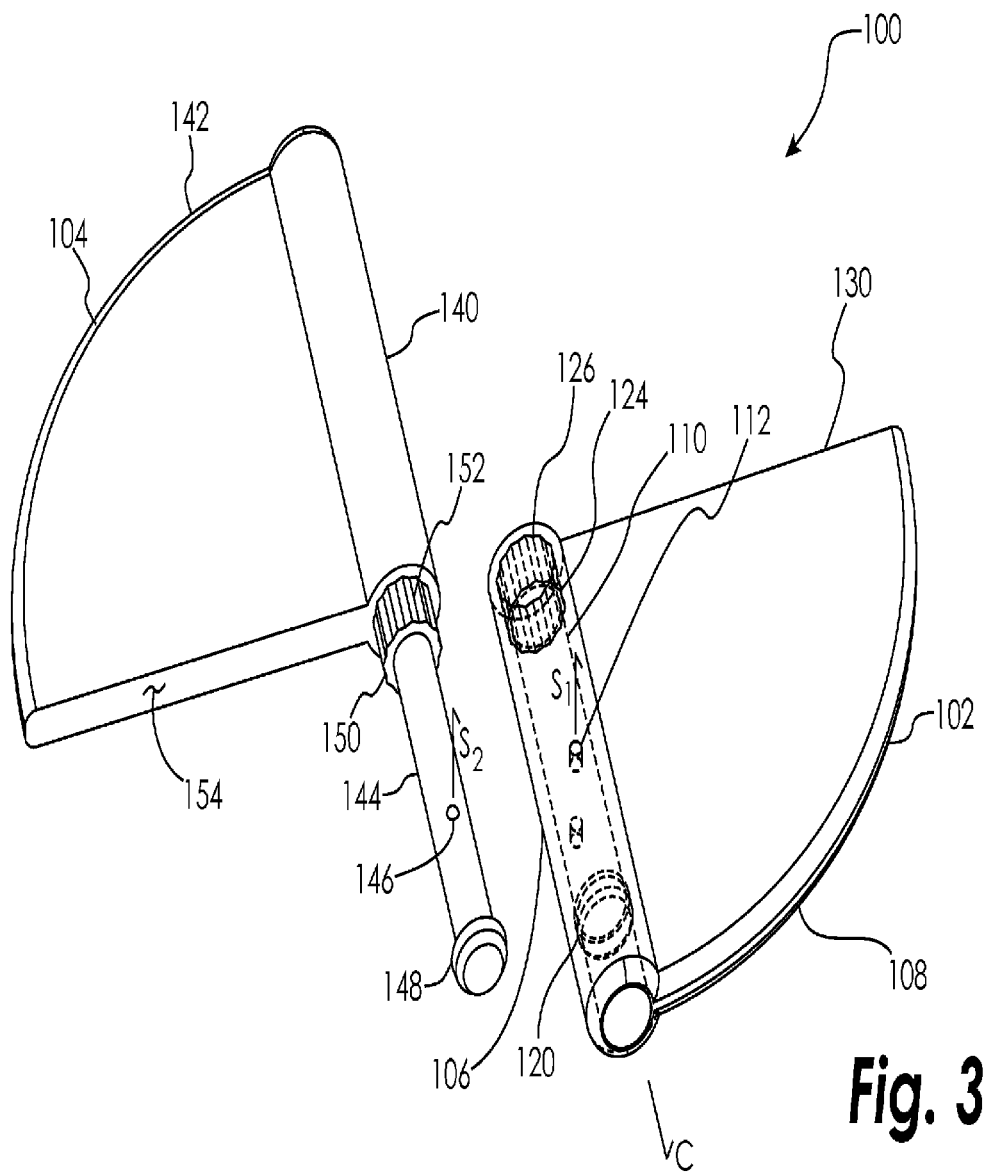
FIG. 3 is yet another perspective view of the medical system of FIG. 1.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

Figure 4:
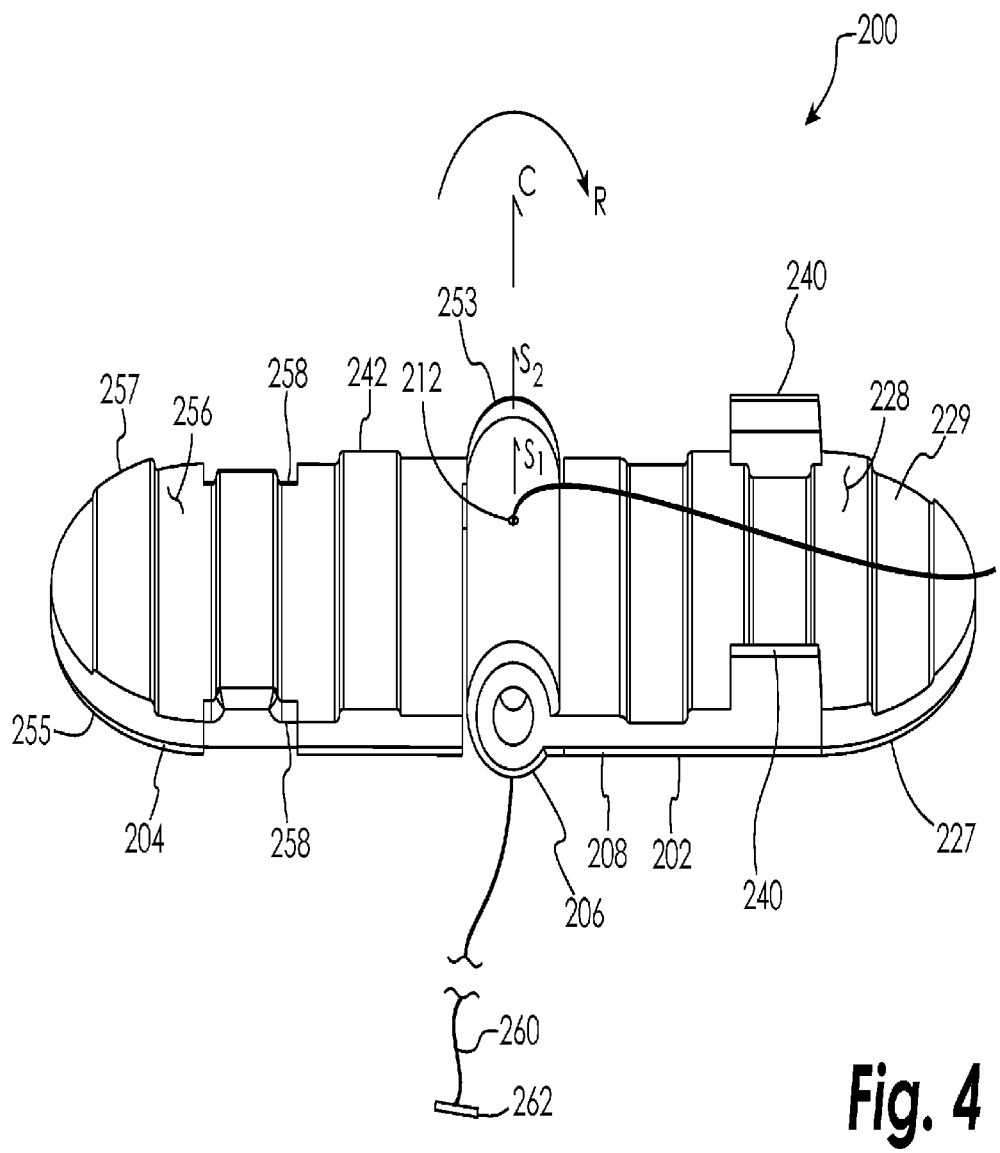
FIG. 4 is a perspective view of an inventive medical system according to another embodiment of the present disclosure.
Figure 5:
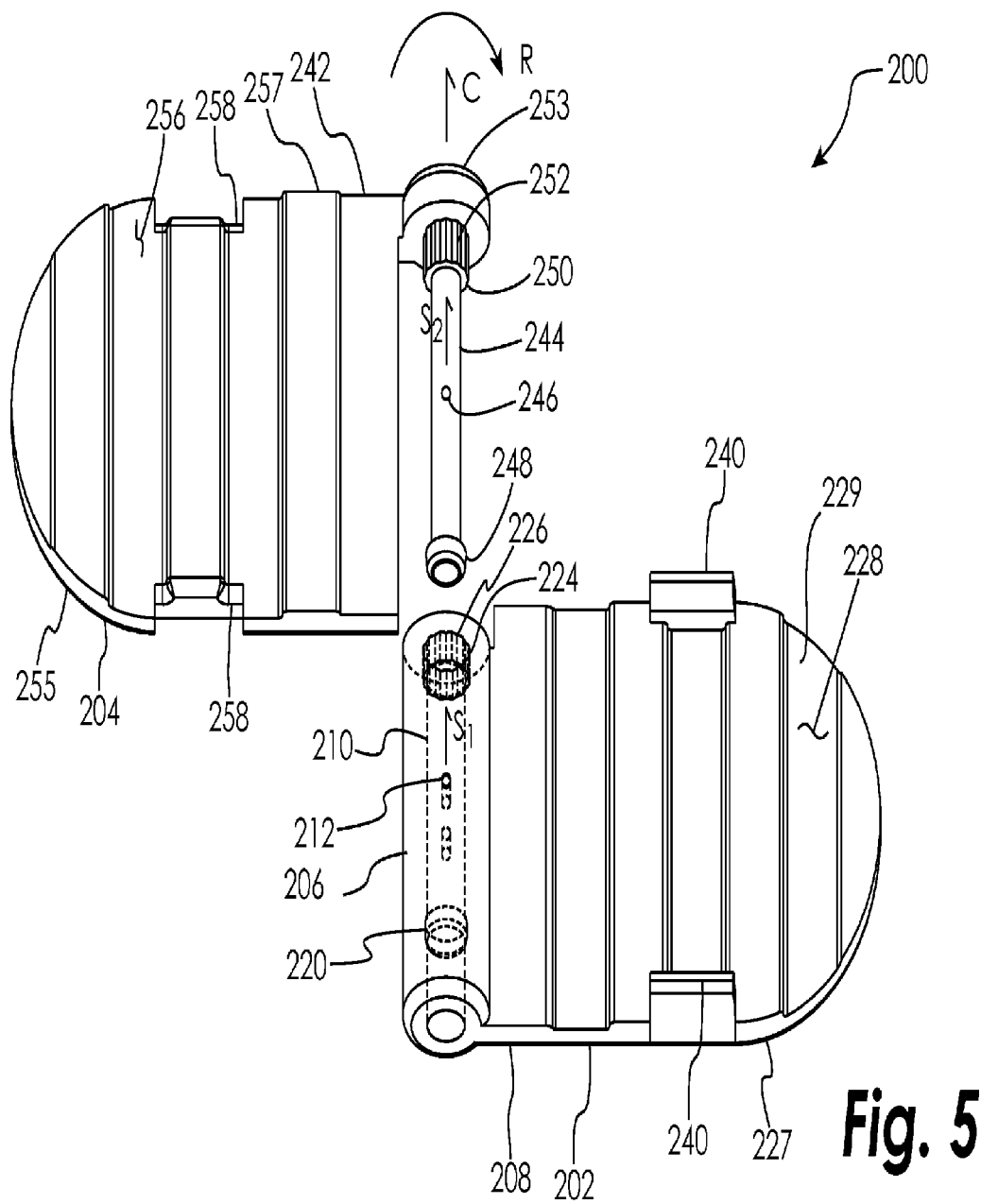
FIG. 5 is another perspective view of the medical system of FIG. 4.
Figure 6:
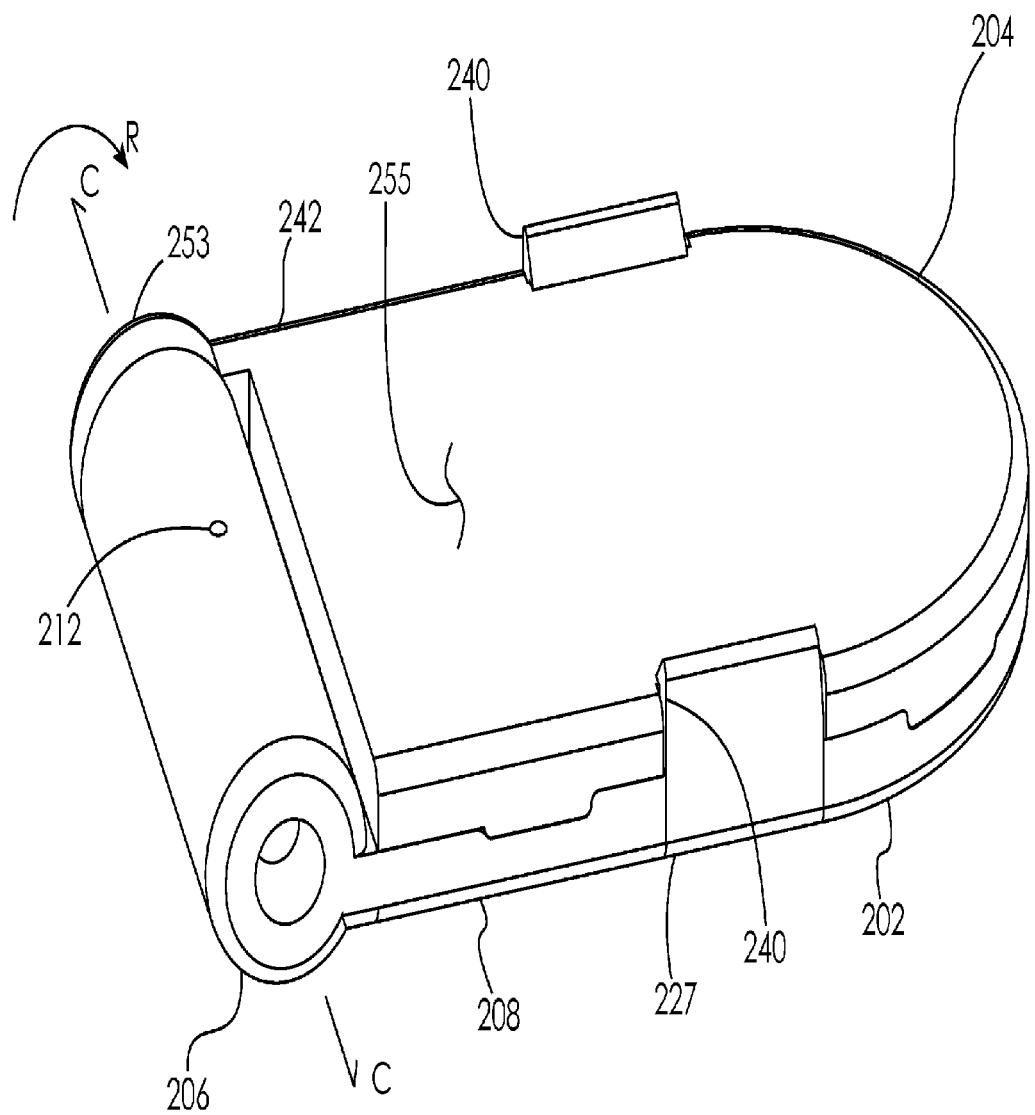
FIG. 6 is yet another perspective view of the medical system of FIG. 4.

In certain aspects, the present disclosure provides unique methods and systems for securing sutures external to the patient's body in a variety of medical procedures. Many medical procedures utilize sutures to engage with and apply tension to anchors or other devices which are positioned within the patient's body. To apply and maintain the appropriate tension force on the anchor, it is necessary to secure the suture material outside of the body. The present disclosure provides for suture securement systems which crimp and/or clamp the suture material to secure it. As used herein, "crimp" is intended to mean bend, pinch, grip, configure in a tortuous path, or similar hold or arrangement. The systems include base paddles, rotating paddles, and in certain embodiments center cylindrical pieces as well. The components define apertures through which a suture may be threaded. Relative movement of the components frictionally crimps the suture along a tortuous path, such that the suture is substantially prevented from moving within the apertures. FIGS. 1 through 3 illustrate one non-limiting example of a suture securement system according to one embodiment of the present disclosure. FIGS. 4 through 6 illustrate another non-limiting example of a suture securement system according to another embodiment of the present disclosure. FIGS. 7 through 10 illustrate yet another non-limiting example of a suture securement system according to yet another embodiment of the present disclosure.

With reference now to FIGS. 1 through 3, there is shown a suture securement system 100 according to one embodiment of the present disclosure. In this illustrative arrangement, a base paddle 102 and a rotating paddle 104 cooperate to frictionally crimp a suture therebetween. The base paddle 102 includes a cylindrical portion 106 adjacent a wing portion 108. The cylindrical portion 106 defines a cylindrical slot 110 in which a portion of the rotating paddle 104 is slideably and rotatably received along a connection axis C (see FIG. 3). Additionally, the cylindrical portion 106 defines a suture aperture 112 configured to receive a suture along a suture axis $S_1$. The suture aperture 112 transects or is otherwise in communication with the slot 110. In the illustrated embodiment, the slot 110 includes an indentation 120 configured to receive a detent or similar mechanism on the rotating paddle 104 to maintain engagement of the paddles.

As best illustrated in FIG. 3, rotating paddle 104 includes a cylindrical portion 140 adjacent a wing portion 142. The rotating paddle 104 further includes an extension arm 144 configured to be slideably received in slot 110 along connection axis C and rotatable therein. The illustrated extension arm 144 defines a suture aperture 146 extending therethrough and configured to receive a suture along a suture axis $S_2$. In certain embodiments, the extension arm 144 may further include a detent mechanism, such as the illustrated resiliently-biased tab 148. The illustrated tab 148 is configured to resiliently flex to allow for advancement of the extension arm 144 within the slot 110, and revert into the indentation 120 upon sufficient advancement of the extension arm 144 in the slot 110 to prevent disengagement of the rotating paddle 104 from the base paddle 102. It should be appreciated that the illustrated arrangement is one non-limiting example of the numerous possible manners of sliding and locking engagement between the rotating paddle 104 and the base paddle 102.

As mentioned above, extension arm 144 is configured to rotate within slot 110 about connection axis C. In certain embodiments, the rotating and base paddles 104 and 102, respectively, may also include a mechanism for locking the paddles at one or more relative rotational positions. As one example, the paddles may incorporate a ratcheting mechanism to provide the relative rotational locking. In the particular illustrated embodiment, the base paddle 102 includes a ratchet mechanism 124 consisting of one or more pivoting, resilient and/or spring-loaded pawls 126, and the illustrated rotating paddle 104 includes a ratchet mechanism 150 consisting of a round portion (e.g. gear or gear-like) with one or more teeth 152 (see FIG. 3). In the illustrated example, the ratchet pawls 126 and teeth 152 are configured to engage each other and allow for rotational movement of extension arm 144 in rotational direction R, while preventing rotational movement back in the opposite direction. In this way, paddle 104 may be rotated in rotational direction R and locked to crimp a suture extending through apertures 112 and 146 to prevent movement of the suture and secure the suture external to the patient's body. It should be appreciated that the illustrated arrangement is one non-limiting example of the numerous possible manners of locking the relative rotational position between the rotating paddle and the base paddle.

Upon sufficient advancement of the extension arm 144 in the slot 110, the suture apertures 112 and 146 are laterally aligned along connection axis C and extension arm 144 may be positioned such that the suture apertures 112 and 146 and the corresponding suture axes $S_1$ and $S_2$ are in axial alignment. In this way, a suture may be threaded through both of the apertures 112 and 146 when the paddles are engaged. In certain embodiments, the paddles 102 and 104 are configured such that when the suture axes $S_1$ and $S_2$ are aligned, the wing portions 108 and 142 are also aligned in a planar arrangement extending in the same direction from connection axis C and the respective adjoining edges 130 and 154 are positioned adjacent and facing each other, as shown in FIG. 1. In certain particular embodiments, the paddles 102 and 104 may be configured such that the respective adjoining edges 130 and 154 are in at least partial contact when the wing portions 108 and 142 are aligned.

It is contemplated that the base paddle 102 and rotating paddle 104, separately and/or collectively, may be shaped and/or sized differently as would occur to one of ordinary skill in the art. Also, specifically, the wing portions 108 and 142 may be shaped differently than as illustrated. In the illustrated embodiment, the wing portions 108 and 142 are substantially quarter-circular in shape in cross section; however, it should be appreciated that the wing portions may be shaped differently, such as full or partial circular, oval, square, triangular or rectangular in cross section.

Additionally, it should be appreciated that the particular elements and features of base paddle 102 and rotating paddle 104 may be configured differently as would occur to one of ordinary skill in the art. As examples, the ratcheting mechanisms 124 and 150 may be positioned at other locations within or along the cylindrical portion 106 and the extension arm 144. As other examples, the indentation 120 and cooperating tab 148 may also be positioned at other locations within or along the cylindrical portion 106 and the extension arm 144. Further, it should be appreciated that the suture apertures 112 and 146 may be positioned and orientated differently, such as angled and oblique to the connection axis C.

With reference to FIGS. 1-3, an example method of securing a suture will be discussed with respect to an example medical procedure requiring the use of a suture and anchor combination. In the illustrated example procedure, a suture 160 is engaged with an anchor 162 in an appropriate manner which is not critical to the present disclosure (see FIG. 1). An introducer needle or other suitable delivery instrument may be used to introduce, deploy and/or secure the suture 160 and anchor 162 combination in the patient's body. The suture and anchor set may be utilized in a variety of medical applications to secure tissue in the body. As one example, one or more suture and anchor sets may be used to secure the patient's stomach to the abdominal or peritoneal wall to allow for insertion and placement of a catheter or other medical device into the patient's stomach. However, it should be appreciated that suture and anchor sets are utilized in a variety of other medical applications. Additionally, it should be appreciated that the suture to be secured may be engaged with a different internally disposed device, or in some applications, the internal device is absent and the suture is directly secured to tissue inside the patient's body.

As part of a typical medical procedure, the suture extends from the anchor or similar device through the patient's body to a point external to the body. The suture is pulled in tension which thereby pulls the anchor firmly against the patient's tissue to be secured. To maintain the tension along the suture, the suture is secured external to the patient's body, for example utilizing system 100.

Prior to use of system 100, rotating paddle 104 is engaged with base paddle 102 by inserting extension arm 144 in slot 110. The resiliently-biased tab 148 on extension arm 144 is configured to resiliently flex during advancement of the extension arm 144 within the slot 110, and then revert into the indentation 120 upon the required advancement of the extension arm 144 in the slot 110 to prevent disengagement of the rotating paddle 104 from the base paddle 102. Upon insertion of extension arm 144, rotating paddle 104 is positioned such that suture apertures 112 and 146 are aligned, with suture axes $S_1$ and $S_2$ thereby also being aligned. Suture apertures 112 and 146 are preferably aligned when wing portions 108 and 142 are substantially planar or otherwise aligned with each other, e.g. with adjoining edges 130 and 154 positioned adjacent each other, as shown in FIG. 1. In this way, the wing portions 108 and 142 together create a handle-type of configuration that a user may more easily grasp when using system 100.

A portion of the suture is threaded through aligned suture apertures 112 and 146. Upon threading, the suture is readily moveable through the apertures. In some embodiments, the base paddle 102, the rotating paddle 104, the suture 160 and the optional anchor 162 may be delivered to a medical professional in a pre-loaded and/or pre-engaged manner prior to use of the system 100, such as the pre-loaded arrangement shown in FIG. 1. After the suture is suitably threaded and the suture and anchor set is positioned within the patient's body as desired, the medical professional using system 100 may adjust the position of the paddles 102 and 104 such that the paddles 102 and 104 are positioned against the patient's skin. It is contemplated that, in certain embodiments, suitable material pieces may optionally be placed between the paddles and the patient's skin to protect the skin and/or provide comfort to the patient.

After the suture 160 is threaded through apertures 112 and 146 and pulled in a significant amount of tension, e.g. with paddles 102 and 104 against or supported by the patient's skin as noted, rotating paddle 104 is rotated about connection axis C along rotational direction R to frictionally crimp the suture within cylindrical portion 106 to secure the suture external to the patient's body. The crimping of the suture prevents or limits suture 160 from moving through the suture apertures 146 and/or 112 and thereby maintains tension along the suture and the associated anchoring device, as necessary to the particular medical procedure being performed. In certain embodiments, paddle 104 may be rotated about 180 degrees so that wing portion 142 is positioned against the patient's skin in a low profile manner (see FIG. 2).

In certain embodiments, ratchet mechanisms 124 and 150 may cooperate to lock the paddles 102 and 104 at one or more relative rotational positions upon rotation of paddle 104 as discussed above. In the particular illustrated embodiment, pawls 126 within slot 110 allow for teeth 152 on extension arm 144 to be rotated in rotational direction R only or principally, preventing or limiting rotational movement in the opposite direction. The ratcheting mechanisms allow for paddle 104 to be rotated and locked at the position shown in FIG. 2 and prevent paddle 104 from returning to the position shown in FIG. 1. As mentioned above, numerous other possible locking mechanisms may be used, as would occur to one of ordinary skill in the art, to secure the relative rotational position of the rotating paddle 104, with the illustrated ratchet mechanisms 124 and 150 being one non-limiting example. In alternative embodiments, a selective locking mechanism may be employed to allow for paddle 104 to be selectively locked at the position shown in FIG. 1 and selectively rotated back to the position shown in FIG. 2 to allow for manipulation of the suture as may be necessary.

In certain embodiments, the rotation of paddle 104 pulls the suture in increased tension and frictionally crimps the suture to secure the suture external to the patient's body. The configuration of paddles 102 and 104 may ensure that little or no manipulation and/or removal of the suture and/or the anchor occurs. In certain embodiments, accessing, manipulating and/or removing the suture and/or the anchor to which the suture is engaged requires cutting the suture at a location between the patient's skin and base paddle 102. In alternative embodiments, paddle 104 may be selectively rotated back (e.g. forced against or over pawls noted above or other mechanisms) to the original threading position (as shown in FIG. 1) to allow for access to or manipulation of the suture. Following the necessary access or manipulation, the rotating paddle 104 may be rotated again along rotational direction R to crimp the suture and secure its position.

With reference now to FIGS. 4 through 6, there is shown a suture securement system 200 according to another embodiment of the present disclosure. In this illustrative arrangement, a base paddle 202 and a rotating paddle 204 cooperate to frictionally crimp a suture therebetween. The base paddle 202 includes a cylindrical portion 206 adjacent a wing portion 208. The cylindrical portion 206 defines a cylindrical slot 210 in which a portion of the rotating paddle 204 is slideably and rotatably received along a connection axis C (see FIG. 5). Additionally, the cylindrical portion 206 defines a suture aperture 212 configured to receive a suture along a suture axis $S_1$. The suture aperture 212 transects or is otherwise in communication with the slot 210. In the illustrated embodiment, the slot 210 includes an indentation 220 configured to receive a detent or similar mechanism on the rotating paddle 204 to maintain engagement of the paddles.

As best illustrated in FIG. 5, rotating paddle 204 includes a wing portion 242 and an extension arm 244 configured to be slideably received in slot 210 along connection axis C and rotatable therein. The illustrated extension arm 244 defines a suture aperture 246 extending therethrough and configured to receive a suture along a suture axis $S_2$. In certain embodiments, the extension arm 244 may further include a detent mechanism, such as the illustrated resiliently-biased tab 248. The illustrated tab 248 is configured to resiliently flex to allow for advancement of the extension arm 244 within the slot 210, and revert into the indentation 220 upon sufficient advancement of the extension arm 244 in the slot 210 to prevent disengagement of the rotating paddle 204 from the base paddle 202. It should be appreciated that the illustrated arrangement is one non-limiting example of the numerous possible manners of sliding and locking engagement between the rotating paddle 204 and the base paddle 202.

As mentioned above, extension arm 244 is configured to rotate within slot 210 about connection axis C. In certain optional embodiments, the rotating and base paddles 204 and 202, respectively, may also include a mechanism for locking the paddles at one or more relative rotational positions. As one example, the paddles may incorporate a ratcheting mechanism to provide the relative rotational locking. In the particular illustrated embodiment, the base paddle 202 includes a ratchet mechanism 224 consisting of one or more pivoting, resilient and/or spring-loaded pawls 226, and the illustrated rotating paddle 204 includes a ratchet mechanism 250 consisting of a round portion (e.g. gear or gear-like) with one or more teeth 252 (see FIG. 5). In the illustrated example, the ratchet pawls 226 and teeth 252 are configured to engage each other and allow for rotational movement of extension arm 244 in rotational direction R, while preventing rotational movement back in the opposite direction. In this way, paddle 204 may be rotated in rotational direction R and locked to crimp a suture extending through apertures 212 and 246 to grip or prevent movement of the suture and secure the suture external to the patient's body. It should be appreciated that the illustrated arrangement is one non-limiting example of the numerous possible manners of locking the relative rotational position between the rotating paddle and the base paddle. In other embodiments, the rotational-locking mechanism, such as ratchet mechanisms 224 and 250, is absent from system 200 and the positioning of the paddles 202 and 204 is secured through other means, such as secured solely by clamp-locking the paddles together, as discussed in greater detail below.

The wing portions 208 and 242 include outer surfaces 227 and 255, respectively, and opposite inner clamping surfaces 228 and 256, respectively. In certain optional embodiments, the inner clamping surfaces 228 and 256 may be configured to at least partially contact each other to clamp a suture therebetween, to assist in the securement of the suture. In further optional embodiments, the inner clamping surfaces 228 and 256 may include a series of mating projections and grooves to further assist in clamping the suture. For example, in the particular illustrated embodiments, inner clamping surface 228 defines a plurality of grooves 229 and inner clamping surface 256 defines a plurality of projections 257 configured to be received in the grooves 229. The illustrated projections 257 and grooves 229 mate together to further crimp the suture. Projections 257 and grooves 229 are shown to be substantially perpendicular to axis C, for ease of manufacture and use and so that the suture can easily cross multiple projections 257 and/or grooves 229. It will be understood that projections 257 and/or grooves 229 may be of different orientation or configuration, such as diagonally or oblique with respect to axis C, or in the form of chevrons.

In such embodiments of system 200 in which the inner surfaces 228 and 256 of wing portions 208 and 242, respectively, are configured to clamp together to assist in securing the suture, system 200 may also include a clamp-locking mechanism to secure the wing portions 208 and 242 clamped together. As one non-limiting example, in the particular illustrated embodiments, wing portion 208 includes two opposing resilient clamping tabs 240 along the edges of the wing portion 208, and wing portion 242 includes two corresponding notches 258 designed to receive the tabs 240. The illustrated tabs 240 are configured to flex and release to engage the wing portion 242 at notches 258 and contact the outer surface 255 to secure the paddles 202 and 204 together at the clamped position. The illustrated tabs 240 and notches 258 may be sized, oriented, and/or arranged differently on the paddles 202 and 204 as would occur to one of ordinary skill in the art. Additionally, it should be appreciated that the illustrated arrangement is one non-limiting example of the numerous possible manners of clamp-locking the rotating paddle 204 and the base paddle 202 together. The clamp-locking mechanism, including the illustrated tabs 240 and notches 258, may be a selective locking mechanism to allow for the paddles 202 and 204 to be selectively locked together at the clamped position shown in FIG. 6 and allow for rotating paddle 204 to be selectively rotated back (e.g. against the force of a ratchet or locking mechanism) to the position shown in FIG. 4 to allow for manipulation of the suture as may be necessary.

It is contemplated that system 200 may include one or both of the rotational locking mechanism, such as the illustrated ratchet mechanisms 224 and 250, and the clamp-locking mechanism, such as the illustrated tabs 240 and corresponding notches 258. In some embodiments, only a rotational-locking mechanism is incorporated into system 200 and, in other embodiments, only a clamp-locking mechanism is incorporated into system 200. In yet other embodiments, other suitable locking mechanisms may be incorporated into system 200, in addition to or in lieu of the locking mechanisms illustrated and discussed herein, as would occur to one of ordinary skill in the art.

Upon sufficient advancement of the extension arm 244 in the slot 210, the suture apertures 212 and 246 are laterally aligned along connection axis C and extension arm 244 may be positioned such that the suture apertures 212 and 246 and the corresponding suture axes $S_1$ and $S_2$ are in axial alignment. In this way, a suture may be threaded through both of the apertures 212 and 246 when the paddles are engaged. In certain embodiments, the paddles 202 and 204 are configured such that when the suture axes $S_1$ and $S_2$ are aligned, the wing portions 208 and 242 are aligned in a planar arrangement extending in substantially opposite directions from connection axis C approximately 180 degrees apart (see FIG. 5). Additionally, in certain optional embodiments, the extension arm 244 includes a cylindrical end cap 253 configured to abut the cylindrical portion 206 upon full advancement of the extension arm 244 in the slot 210.

It is contemplated that the base paddle 202 and rotating paddle 204, separately and/or collectively, may be shaped and/or sized differently as would occur to one of ordinary skill in the art. Also, specifically, the wing portions 208 and 242 may be shaped differently than as illustrated, such as full or partial circular, oval, square, triangular or rectangular in cross section. Additionally, it should be appreciated that the particular elements and features of base paddle 202 and rotating paddle 204 may be configured differently as would occur to one of ordinary skill in the art. As examples, the ratcheting mechanisms 224 and 250 may be positioned at other locations within or along the cylindrical portion 206 and the extension arm 244. As other examples, the indentation 220 and cooperating tab 248 may also be positioned at other locations within or along the cylindrical portion 206 and the extension arm 244. Further, it should be appreciated that the suture apertures 212 and 246 may be positioned and orientated differently, such as angled and oblique to the connection axis C.

With reference to FIGS. 4-6, an example method of securing a suture will be discussed with respect to an example medical procedure requiring the use of a suture and anchor combination. In the illustrated example procedure, which is similar to that described above, a suture 260 is engaged with an anchor 262 in an appropriate manner which is not critical to the present disclosure (see FIG. 4). An introducer needle or other suitable delivery instrument may be used to introduce, deploy and/or secure the suture 260 and anchor 262 combination in the patient's body. The suture and anchor set may be utilized in a variety of medical applications to secure tissue in the body. As one example, one or more suture and anchor sets may be used to secure the patient's stomach to the abdominal or peritoneal wall to allow for insertion and placement of a catheter or other medical device into the patient's stomach. However, it should be appreciated that suture and anchor sets are utilized in a variety of other medical applications. Additionally, it should be appreciated that the suture to be secured may be engaged with a different internally disposed device, or in some applications, the internal device is absent and the suture is directly secured to tissue inside the patient's body.

As part of a typical medical procedure, the suture extends from the anchor or similar device through the patient's body to a point external to the body. The suture is pulled in tension which thereby pulls the anchor firmly against the patient's tissue to be secured. To maintain the tension along the suture, the suture is secured external to the patient's body, for example utilizing system 200.

Prior to use of system 200, rotating paddle 204 is engaged with base paddle 202 by inserting extension arm 244 in slot 210. The resiliently-biased tab 248 on extension arm 244 is configured to resiliently flex during advancement of the extension arm 244 within the slot 210, and then revert into the indentation 220 upon the required advancement of the extension arm 244 in the slot 210 to prevent disengagement of the rotating paddle 204 from the base paddle 202. Upon insertion of extension arm 244, rotating paddle 204 is positioned such that suture apertures 212 and 246 are aligned, with suture axes $S_1$ and $S_2$ thereby also being aligned. Suture apertures 212 and 246 are preferably aligned such that wing portions 208 and 242 extend in substantially opposite directions from connection axis C in a low profile manner, as shown in FIG. 4.

A portion of the suture is threaded through aligned suture apertures 212 and 246. Upon threading, the suture is readily moveable through the apertures. In some embodiments, the base paddle 202, the rotating paddle 204, the suture 260 and the optional anchor 262 may be delivered to a medical professional in a pre-loaded and/or pre-engaged manner prior to use of the system 200, such as the pre-loaded arrangement shown in FIG. 4. After the suture is suitably threaded and the suture and anchor set is positioned within the patient's body as desired, the medical professional using system 200 may adjust the position of the paddles 202 and 204 such that the paddles 202 and 204 are positioned against the patient's skin. It is contemplated that, in certain embodiments, suitable material pieces may optionally be placed between the paddles and the patient's skin to protect the skin and/or provide comfort to the patient.

After the suture is threaded through apertures 212 and 246 and pulled in a substantial amount of tension, rotating paddle 204 is rotated about connection axis C along rotational direction R to frictionally crimp the suture within cylindrical portion 206 to assist in securing the suture external to the patient's body. The crimping of the suture prevents or limits the suture from moving through the suture apertures 212 and 246 and thereby maintains tension along the suture and the associated anchoring device, as necessary to the particular medical procedure being performed. In certain embodiments, paddle 204 may be rotated about 180 degrees so that wing portion 242 is positioned on top of wing portion 208 in a low profile manner (see FIG. 6).

In certain embodiments, the optional ratchet mechanisms 224 and 250 may cooperate to lock the paddles 202 and 204 at one or more relative rotational positions upon rotation of paddle 204 as discussed above. In the particular illustrated embodiment, pawls 226 within slot 210 allow for teeth 252 on extension arm 244 to be rotated in rotational direction R only or principally, while limiting or preventing rotational movement in the opposite direction. The ratcheting mechanisms allow for paddle 204 to be rotated and locked at the position shown in FIG. 6 and prevent paddle 204 from returning to the position shown in FIG. 4. As mentioned above, numerous other possible rotational-locking mechanisms may be used, as would occur to one of ordinary skill in the art, to secure the relative rotational position of the rotating paddle 204, with the illustrated ratchet mechanisms 224 and 250 being one non-limiting example. Additionally, it is contemplated that the rotational-locking mechanism may be absent in certain embodiments and the positioning of the paddles 202 and 204 is solely secured by locking the paddles together at the clamped position shown in FIG. 6.

In certain embodiments, upon rotation of rotating paddle 204 along rotational direction R to meet base paddle 202, the paddles 202 and 204 may be configured to clamp together to assist in securing the suture. In such embodiments, a suture extending from aperture 212 may be positioned between the wing portions 208 and 242, with the inner surfaces 228 and 256 clamping together to assist in securing the suture external to the patient's body. The optional projections 257 and corresponding grooves 229 cooperate to crimp the suture between the clamping surfaces 228 and 256 to further assist in securing the suture. As discussed above, system 200 may include a clamp-locking mechanism to secure the wing portions 208 and 242 clamped together. In the particular illustrated embodiments, tabs 240 are configured to engage wing portion 242 at notches 258 to secure the wing portions 208 and 242 clamped together, as shown in FIG. 6.

In certain embodiments, the rotation of paddle 204 pulls the suture in increased tension and/or draws in a portion of the suture outside the patient, and frictionally crimps the suture to secure the suture external to the patient's body. Additionally, the wing portions 208 and 242 may be clamped together with the suture extending therebetween to further assist in securing the suture. The configuration of paddles 202 and 204 may ensure that little or no manipulation and/or removal of the suture and/or the anchor occurs. In certain embodiments, accessing, manipulating and/or removing the suture and/or the anchor to which the suture is engaged requires cutting the suture at a location between the patient's skin and base paddle 202. In alternative embodiments, paddle 204 may be selectively rotated back (e.g. against the force of ratchet or locking mechanisms) to the original threading position (as shown in FIG. 4) to allow for access to or manipulation of the suture. Following the necessary access or manipulation, the rotating paddle 204 may be rotated again along rotational direction R to crimp the suture and secure its position.

With reference now to FIGS. 7 through 10, there is shown a suture securement system 300 according to another embodiment of the present disclosure. In this illustrative arrangement, a base paddle 302, a rotating paddle 304 and a central cylindrical sleeve 305 cooperate to frictionally crimp a suture therebetween. The base paddle 302 includes a cylindrical portion 306 adjacent a wing portion 308. The cylindrical portion 306 defines a cylindrical slot 310 in which a portion of the rotating paddle 304 is slideably and rotatably received along a connection axis C (see FIG. 8). Additionally, the cylindrical portion 306 defines a suture aperture 312 configured to receive a suture along a suture axis $S_1$. The suture aperture 312 transects or is otherwise in communication with the slot 310. In the illustrated embodiment, the slot 310 includes an indentation 320 configured to receive a detent or similar mechanism on the rotating paddle 304 to maintain engagement of the paddles.

Figure 8:
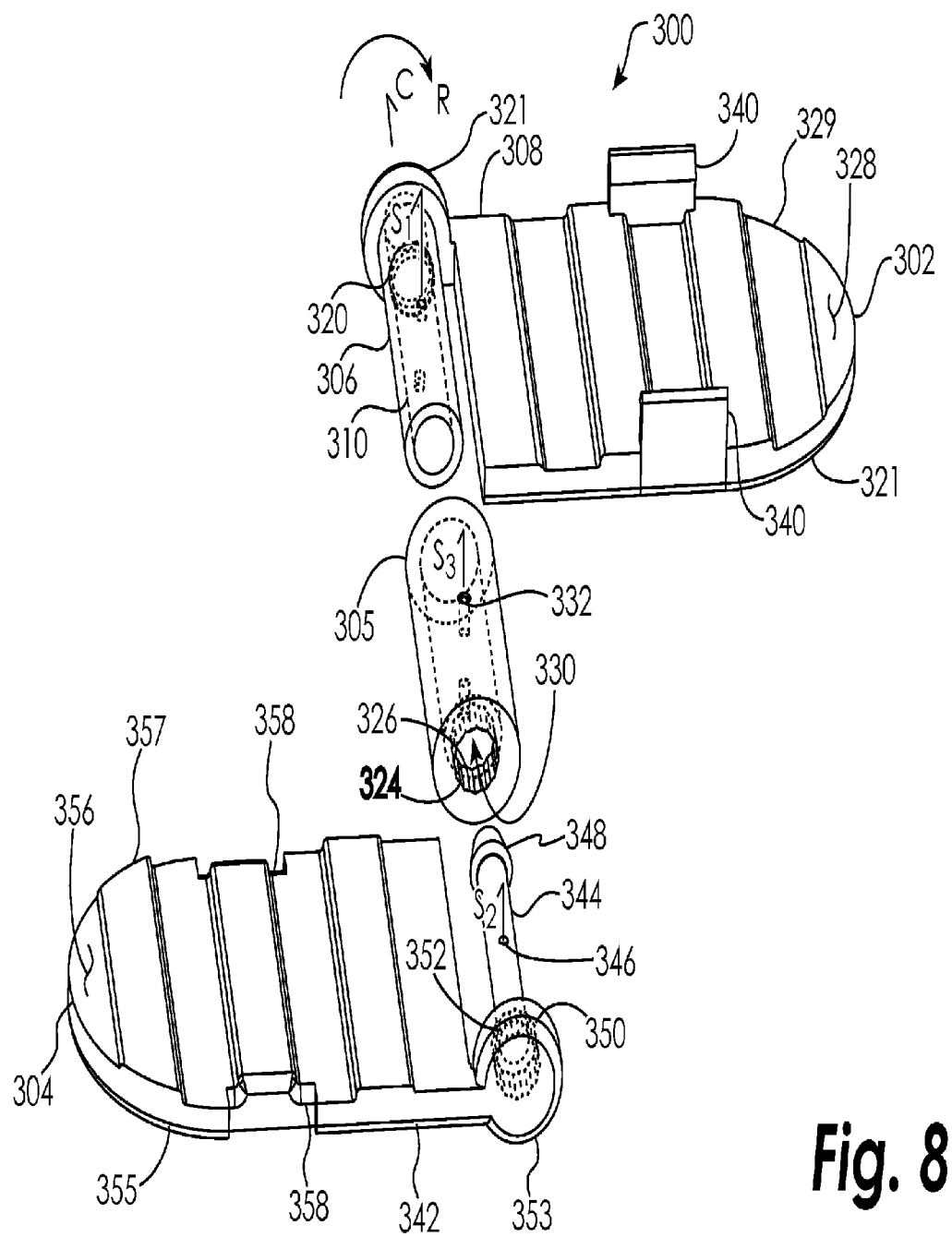
FIG. 8 is another perspective view of the medical system of FIG. 7.

As best illustrated in FIG. 8, rotating paddle 304 includes a wing portion 342 and an extension arm 344 configured to be slideably received in slot 310 along connection axis C and rotatable therein. The illustrated extension arm 344 defines a suture aperture 346 extending therethrough and configured to receive a suture along a suture axis $S_2$. In certain embodiments, the extension arm 344 may further include a detent mechanism, such as the illustrated resiliently-biased tab 348. The illustrated tab 348 is configured to resiliently flex to allow for advancement of the extension arm 344 within the slot 310, and revert into the indentation 320 upon sufficient advancement of the extension arm 344 in the slot 310 to prevent disengagement of the rotating paddle 304 from the base paddle 302. It should be appreciated that the illustrated arrangement is one non-limiting example of the numerous possible manners of sliding and locking engagement between the rotating paddle 304 and the base paddle 302.

The illustrated system 300 further includes a hollow, center cylindrical sleeve 305 to assist in the securement of the suture. As best illustrated in FIG. 8, sleeve 305 defines a cylindrical slot 330 in which the cylindrical portion 306 and the extension arm 344 are slidably and rotatably received along the connection axis C. Additionally, the sleeve 305 defines a suture aperture 332 configured to receive a suture along a suture axis $S_3$. The suture aperture 332 transects or is otherwise in communication with the slot 330.

As mentioned above, extension arm 344 is configured to rotate within slot 310 and cylindrical portion 306 is configured to rotate within slot 330 about connection axis C. In certain optional embodiments, one or more of the base paddle 302, rotating paddle 304 and/or cylindrical sleeve 305 may also include a mechanism for locking or holding the components at one or more relative rotational positions. As one example, the rotating paddle 304 and the cylindrical sleeve 305 may incorporate a ratcheting mechanism to provide the relative rotational locking. In the particular illustrated embodiment, the cylindrical sleeve 305 includes a ratchet mechanism 324 consisting of one or more pivoting, resilient and/or spring-loaded pawls 326, and the illustrated rotating paddle 304 includes a ratchet mechanism 350 consisting of a round portion (e.g. gear or gear-like) with one or more teeth 352 (see FIG. 8). In the illustrated example, the ratchet pawls 326 and teeth 352 are configured to engage each other and allow for rotational movement of extension arm 344 in rotational direction R, while preventing rotational movement back in the opposite direction. In this way, paddle 304 may be rotated in rotational direction R and locked to crimp a suture extending through apertures 312 and 346 to prevent or limit movement of the suture and secure the suture external to the patient's body.

In certain embodiments, rotating paddle 304 may be clamped and locked together with base paddle 302, as discussed in greater detail below, such that both of the base and rotating paddles 302 and 304, respectively, rotate together with respect to cylindrical sleeve 305 and may be locked at relative rotational positions via the ratcheting mechanisms. It should be appreciated that the illustrated arrangement is one non-limiting example of the numerous possible manners of locking the relative rotational position between the components of system 300. In other embodiments, the rotational-locking mechanism, such as ratchet mechanisms 324 and 350, is absent from system 300 and the positioning of the paddles 302 and 304 is secured by other means, such as through clamp-locking the paddles together, as discussed in greater detail below.

The wing portions 308 and 342 include outer surfaces 327 and 355, respectively, and opposite inner clamping surfaces 328 and 356, respectively. In certain optional embodiments, the inner clamping surfaces 328 and 356 may be configured to at least partially contact each other to clamp a suture therebetween, to assist in the securement of the suture. In further optional embodiments, the inner clamping surfaces 328 and 356 may include a series of mating projections and grooves to further assist in clamping the suture. For example, in the particular illustrated embodiments, inner clamping surface 328 defines a plurality of grooves 329 and inner clamping surface 356 defines a plurality of projections 357 configured to be received in the grooves 329. The illustrated projections 357 and grooves 329 mate together to further crimp the suture. As noted in an earlier example, t will be understood that projections 357 and/or grooves 329 may be of different orientation or configuration, such as diagonally or oblique with respect to axis C, or in the form of chevrons.

In such embodiments of system 300 in which the inner surfaces 328 and 356 of wing portions 308 and 342, respectively, are configured to clamp together to assist in securing the suture, system 300 may also include a clamp-locking mechanism to secure the wing portions 308 and 342 clamped together. As one non-limiting example, in the particular illustrated embodiments, wing portion 308 includes two opposing resilient clamping tabs 340 along the edges of the wing portion 308, and wing portion 342 includes two corresponding notches 358 designed to receive the tabs 340. The illustrated tabs 340 are configured to flex and release to engage the wing portion 342 at notches 358 and contact the outer surface 355 to secure the paddles 302 and 304 together at the clamped position. The illustrated tabs 340 and notches 358 may be sized, oriented, and/or arranged differently on the paddles 302 and 304 as would occur to one of ordinary skill in the art. Additionally, it should be appreciated that the illustrated arrangement is one non-limiting example of the numerous possible manners of clamp-locking the rotating paddle 304 and the base paddle 302 together. The clamp-locking mechanism, including the illustrated tabs 340 and notches 358, may be a selective locking mechanism to allow for the paddles 302 and 304 to be selectively locked together at the clamped position shown in FIGS. 9 and 10 and allow for rotating paddle 304 to be selectively rotated back to the position shown in FIG. 7 to allow for manipulation of the suture as may be necessary.

It is contemplated that system 300 may include one or both of the rotational locking mechanism, such as the illustrated ratchet mechanisms 324 and 350, and the clamp-locking mechanism, such as the illustrated tabs 340 and corresponding notches 358. In some embodiments, only a rotational-locking mechanism is incorporated into system 300 and, in other embodiments, only a clamp-locking mechanism is incorporated into system 300. In yet other embodiments, other suitable locking mechanisms may be incorporated into system 300, in addition to or in lieu of the locking mechanisms illustrated and discussed herein, as would occur to one of ordinary skill in the art.

Upon sufficient advancement of the extension arm 344 in the slot 310 and sufficient advancement of the cylindrical portion 306 in slot 330, the suture apertures 312, 346 and 332 are laterally aligned along connection axis C and the components may be positioned such that the suture apertures and the corresponding suture axes $S_1$, $S_2$ and $S_3$ are in axial alignment. In this way, a suture may be threaded through all of the apertures 312, 346 and 332 when the components are engaged. In certain embodiments, the paddles 302 and 304 and the sleeve 305 are configured such that when the suture axes $S_1$, $S_2$ and $S_3$ are aligned, the wing portions 308 and 342 are aligned in a planar arrangement extending in substantially opposite directions from connection axis C approximately 180 degrees apart (see FIG. 7). Additionally, in certain optional embodiments, the extension arm 344 includes a cylindrical end cap 353 and the cylindrical portion 306 includes a cylindrical end cap 321 configured to abut the edges of cylindrical sleeve 305 upon full engagement of the components.

It is contemplated that the base paddle 302, rotating paddle 304 and/or sleeve 305, separately and/or collectively, may be shaped and/or sized differently as would occur to one of ordinary skill in the art. Also, specifically, the wing portions 308 and 342 may be shaped differently than as illustrated, such as full or partial circular, oval, square, triangular or rectangular in cross section. Additionally, it should be appreciated that the particular elements and features of base paddle 302, rotating paddle 304 and/or sleeve 305 may be configured differently as would occur to one of ordinary skill in the art. As examples, the ratcheting mechanisms 324 and 350 may be positioned at other locations within or along the sleeve 305 and the extension arm 344. As other examples, the indentation 320 and cooperating tab 348 may also be positioned at other locations within or along the cylindrical portion 306 and the extension arm 344. Further, it should be appreciated that the suture apertures 312, 346 and 332 may be positioned and orientated differently, such as angled and oblique to the connection axis C.

With reference to FIGS. 7-10, an example method of securing a suture will be discussed with respect to an example medical procedure requiring the use of a suture and anchor combination. In the illustrated example procedure, a suture 360 is engaged with an anchor 362 in an appropriate manner which is not critical to the present disclosure (see FIG. 7). An introducer needle or other suitable delivery instrument may be used to introduce, deploy and/or secure the suture 360 and anchor 362 combination in the patient's body. The suture and anchor set may be utilized in a variety of medical applications to secure tissue in the body. As one example, one or more suture and anchor sets may be used to secure the patient's stomach to the abdominal or peritoneal wall to allow for insertion and placement of a catheter or other medical device into the patient's stomach. However, it should be appreciated that suture and anchor sets are utilized in a variety of other medical applications. Additionally, it should be appreciated that the suture to be secured may be engaged with a different internally disposed device, or in some applications, the internal device is absent and the suture is directly secured to tissue inside the patient's body.

As part of a typical medical procedure, the suture extends from the anchor or similar device through the patient's body to a point external to the body. The suture is pulled in tension which thereby pulls the anchor firmly against the patient's tissue to be secured. To maintain the tension along the suture, the suture is secured external to the patient's body, for example utilizing system 300.

Figure 7:
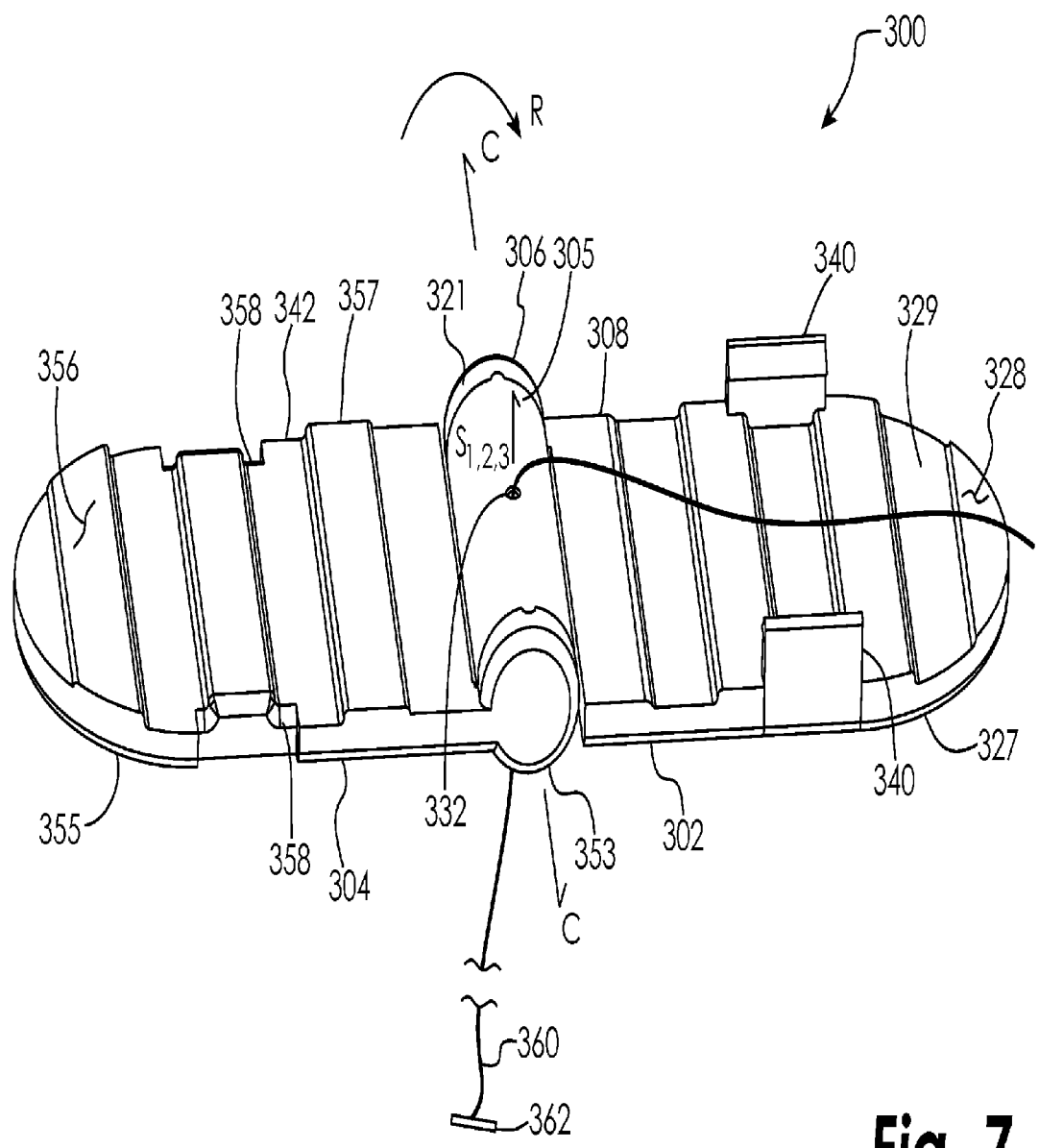
FIG. 7 is a perspective view of an inventive medical system according to another embodiment of the present disclosure.

Prior to use of system 300, the base paddle 302, the rotating paddle 304 and the cylindrical sleeve 305 are engaged with each other by cylindrical portion 306 in slot 330 and inserting extension arm 344 in slot 310. The resiliently-biased tab 348 on extension arm 344 is configured to resiliently flex during advancement of the extension arm 344 within the slot 310, and then revert into the indentation 320 upon the required advancement of the extension arm 344 in the slot 310 to prevent disengagement of the rotating paddle 304 from the base paddle 302. Accordingly, the paddles 302 and 304 are also prevented from disengaging with sleeve 305. Upon engagement of the components, base paddle 302, rotating paddle 304 and sleeve 305 are positioned such that suture apertures 312, 346 and 332 are aligned, with suture axes $S_1$, $S_2$ and $S_3$ thereby also being aligned. Suture apertures 312, 346 and 332 are preferably aligned such that wing portions 308 and 342 extend in substantially opposite directions from connection axis C in a low profile manner, as shown in FIG. 7.

A portion of the suture is threaded through aligned suture apertures 312, 346 and 332. Upon threading, the suture is readily moveable through the apertures. In some embodiments, the base paddle 302, the rotating paddle 304, the sleeve 305, the suture 360 and the optional anchor 362 may be delivered to a medical professional in a pre-loaded and/or pre-engaged manner prior to use of the system 300, such as the pre-loaded arrangement shown in FIG. 7. After the suture is suitably threaded and the suture and anchor set is positioned within the patient's body as desired, the medical professional using system 300 may adjust the position of the paddles 302 and 304 and sleeve 305 such that the paddles 302 and 304 and sleeve 305 are positioned against the patient's skin. It is contemplated that, in certain embodiments, suitable material pieces may optionally be placed between the paddles and/or sleeve and the patient's skin to protect the skin and/or provide comfort to the patient.

After the suture is threaded through apertures 312, 346 and 332 and pulled in a substantial amount of tension, rotating paddle 304 is rotated about connection axis C along rotational direction R to frictionally crimp the suture within cylindrical portion 306 to assist in securing the suture external to the patient's body. In certain embodiments, base paddle 302 may also be rotated to assist in crimping the suture, with base paddle 302 rotating in a direction opposite from rotational direction R. As an example route, both paddles 302 and 304 may be rotated about 90 degrees such that the paddles meet in a substantially vertical orientation (see FIG. 9). At such point the paddles 302 and 304 may then be optionally clamped together, as discussed in greater detail below, and rotated together to the substantially horizontal orientation shown in FIG. 10. In certain other embodiments, paddle 302 may remain in the horizontal position shown in FIG. 7 while paddle 304 is rotated about 180 degrees so that wing portion 342 is positioned on top of wing portion 308 in a low profile manner (see FIG. 10). In such embodiments, the arrangement shown in FIG. 9 does not occur. In any of the contemplated routes of rotation by one or both of the paddles 302 and 304, the suture is crimped to prevent the suture from moving through the suture apertures 312, 346 and 332, thereby maintaining tension along the suture and the associated anchoring device as necessary to the particular medical procedure being performed.

In certain embodiments, the optional ratchet mechanisms 324 and 350 may cooperate to lock the paddles 302 and 304 at one or more relative rotational positions upon rotation of paddle 304 (and optionally paddle 302) as discussed above. In the particular illustrated embodiment, pawls 326 within slot 310 allow for teeth 352 on extension arm 344 to be rotated in rotational direction R only, while preventing rotational movement in the opposite direction. The ratcheting mechanisms allow for paddle 304 (and paddle 302 clamped thereto) to be rotated and locked at the position shown in FIG. 10 and prevent paddle 304 from returning to the position shown in FIG. 7. As mentioned above, numerous other possible rotational-locking mechanisms may be used, as would occur to one of ordinary skill in the art, to secure the relative rotational position of the rotating paddle 304, with the illustrated ratchet mechanisms 324 and 350 being one non-limiting example. Additionally, it is contemplated that the rotational-locking mechanism may be absent in certain embodiments and the positioning of the paddles 302 and 304 is solely secured by locking the paddles together at the clamped position shown in FIGS. 9 and/or 10.

In certain embodiments, upon rotation of rotating paddle 304 along rotational direction R to meet base paddle 302, the paddles 302 and 304 may be configured to clamp together to assist in securing the suture. In such embodiments, a suture extending from aperture 312 may be positioned between the wing portions 308 and 342, with the inner surfaces 328 and 356 clamping together to assist in securing the suture external to the patient's body. The optional projections 357 and corresponding grooves 329 cooperate to crimp the suture between the clamping surfaces 328 and 356 to further assist in securing the suture. As discussed above, system 300 may include a clamp-locking mechanism to secure the wing portions 308 and 342 clamped together. In the particular illustrated embodiments, tabs 340 are configured to engage wing portion 342 at notches 358 to secure the wing portions 308 and 342 clamped together, as shown in FIGS. 9 and 10. In the particular illustrated embodiments, paddles 302 and 304 are clamped and locked together in the substantially vertical orientation shown in FIG. 9 and rotated together along rotational direction R to the substantial horizontal orientation shown in FIG. 10.

In certain embodiments, the rotation of paddle 304 (and paddle 302 in the illustrated embodiments) pulls the suture in increased tension and frictionally crimps the suture to secure the suture external to the patient's body. Additionally, the wing portions 308 and 342 may be clamped together with the suture extending therebetween to further assist in securing the suture. The configuration of paddles 302 and 304 and sleeve 305 may ensure that little or no manipulation and/or removal of the suture and/or the anchor occurs. In certain embodiments, accessing, manipulating and/or removing the suture and/or the anchor to which the suture is engaged requires cutting the suture at a location between the patient's skin and sleeve 305. In alternative embodiments, paddle 304 may be selectively rotated back to the original threading position (as shown in FIG. 7) to allow for access to or manipulation of the suture. Following the necessary access or manipulation, the rotating paddle 304 and base paddle 302 may be manipulated again as discussed above to crimp the suture and secure its position.

In certain embodiments, the systems discussed herein may be utilized in multiple to secure multiple sutures to allow for the insertion and placement of a catheter or other medical device. In such embodiments, the catheter is inserted centrally between the multiple systems and sutures within a catheter placement zone. In a particular example embodiment, three system and sutures are arranged in a triangular pattern, with the catheter being inserted centrally between the triangular arrangement of suture securement systems. It is contemplated that at least system 200 and 300 may provide for an increased placement zone for a catheter or similar device, owing to the sutures being located toward an edge of the paddles, as opposed to the sutures being more centrally positioned with respect to the paddles. In this way, less of the paddles are positioned such that they would interfere with the placement zone of the catheter.

The components of systems 100, 200 and 200 may be formed with a variety of biocompatible polymer materials. As examples, one or more of the components may be made of polypropylene, polyethylene or similar suitable materials. Regarding sutures 160, 260 and 360, while suture material in particular will be useful in certain inventive embodiments, a variety of other elongate materials and objects capable of being anchored can be used as an alternative to, or in addition, to suture material. These include various types of cords, filaments, chains, strings, wires and other similar objects having relatively slender profiles for extending through patient tissue.

Any or all of the components described herein can be provided in a sterile pack for providing necessary parts, or a variety of parts, to a surgeon. For example, one or more predetermined types or sizes of introducer needle, engaged suture and anchor combination, and suture securement system may be provided in a single sterile package or kit. A surgeon can choose the sizes or types of components he or she wishes to use during surgery. Alternatively, sterile kits containing predetermined sizes or types of components may be provided. Packages or kits of the components described herein can include additional devices or tools which may be useful in the particular medical procedure being performed.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the disclosures as defined herein or by the following claims are desired to be protected. It will be understood that features described particularly with respect to one or more specific structures or embodiments may be incorporated into or otherwise used with other structures or embodiments as disclosed herein.

What is claimed is:

1. An external suture securement apparatus, comprising:
   a base paddle having a wing portion and defining a slot extending at least partially through the base paddle, wherein the base paddle defines a suture aperture extending therethrough and being adapted to receive a suture, wherein the suture aperture is in communication with and extends transversely through the slot; and
   a rotating paddle having a wing portion and an extension arm rotatably received in the slot along a connection axis, wherein the extension arm defines a suture aperture extending therethrough and being adapted to receive a suture, wherein the extension arm is configured to rotate in the slot to frictionally crimp a suture extending through the suture apertures, wherein the extension arm includes a detent mechanism configured to maintain positioning of the extension arm in the slot and prevent disengagement of the rotating paddle from the base paddle;
   wherein at least one of the base paddle and the rotating paddle includes a locking mechanism configured to lock the rotational position of the rotating paddle with respect to the base paddle;
   wherein, in an uncrimped configuration, the suture apertures in the base paddle and the rotating paddle are in axial alignment such that the suture is freely moveable within the apertures, and wherein the wing portions of the base paddle and the rotating paddle extend from the connection axis,
   wherein, in a crimped configuration, the suture apertures in the base paddle and the rotating paddle frictionally crimp a suture within the slot such that the suture is substantially prevented from moving within the apertures, and wherein the wing portions of the base paddle and the rotating paddle are configured to be locked in position via the locking mechanism.

2. The apparatus of claim 1, wherein the slot includes an indentation and the detent mechanism includes a resiliently-biased tab configured to resiliently flex and revert into the indentation upon full advancement of the extension arm in the slot.

3. The apparatus of claim 1, wherein the suture apertures in the base paddle and the rotating paddle each extend along a suture axis perpendicular to the connection axis.

4. The apparatus of claim 1, wherein the locking mechanism includes a first mating locking piece on the base paddle and a second mating locking piece on the rotating paddle, the mating locking pieces cooperatively defining a ratchet mechanism.

5. The apparatus of claim 4, wherein the ratchet mechanism includes a round portion with one or more teeth positioned on the extension arm and one or more pivoting pawls included on the base paddle within the slot configured to engage the teeth.

6. The apparatus of claim 1, further comprising a suture extending through the suture apertures of the base paddle and the rotating paddle, and further comprising a suture anchor engaged with the suture.

7. The apparatus of claim 1, wherein in the uncrimped configuration, the wing portions of the base paddle and the rotating paddle extend in substantially the opposite direction from the connection axis.

8. The apparatus of claim 1, wherein in the uncrimped configuration, the wing portions of the base paddle and the rotating paddle extend in substantially the same direction from the connection axis.

9. The apparatus of claim 1, wherein each of the wing portions includes an inside clamping surface, wherein the wing portions are configured to be pressed together to clamp the suture between the inside clamping surfaces.

10. The apparatus of claim 9, wherein the inside clamping surfaces include corresponding pairs of projections and grooves configured to assist in clamping the suture between the inside clamping surfaces.

11. The apparatus of claim 1, wherein at least one of the wing portions of the base paddle and the rotating paddle includes a clamp-locking mechanism configured to lock the wing portions pressed together.

12. The apparatus of claim 11, wherein the wing portions of the base paddle and the rotating paddle are clamped together extending in substantially the same direction from the connection axis to clamp the suture therebetween, and wherein the base paddle and the rotating paddle clamped together are rotated with respect to the cylindrical sleeve and locked at the desired position via the locking mechanism.

13. An external suture securement apparatus, comprising:
a first paddle having a wing portion and defining a slot extending at least partially through the first paddle, wherein the first paddle defines a suture aperture extending therethrough and being adapted to receive a suture, wherein the suture aperture is in communication with and extends transversely through the slot; and
a second paddle having a wing portion and an extension arm rotatably received in the slot along a connection axis, wherein the extension arm defines a suture aperture extending therethrough and being adapted to receive a suture.

14. The apparatus of claim 13, wherein the extension arm includes a detent mechanism configured to maintain positioning of the extension arm in the slot.

15. The apparatus of claim 14, wherein an indentation is included in one of the slot and the extension arm, and the detent mechanism includes a resiliently-biased tab in the other of the slot and the extension arm, the tab configured to enter the indentation upon full advancement of the extension arm in the slot.

16. The apparatus of claim 13, wherein at least one of the first paddle and the second paddle includes a locking mechanism configured to lock the rotational position of the paddles with respect to each other.

17. The apparatus of claim 13, wherein in an uncrimped configuration, the suture apertures in the first paddle and the second paddle are in axial alignment such that the suture is freely moveable within the apertures, and in a crimped configuration, the suture apertures in the first paddle and the second paddle frictionally crimp a suture within the slot such that the suture is substantially prevented from moving within the apertures.

18. The apparatus of claim 13, wherein in an uncrimped configuration, the wing portion of the first paddle extends to one side of the connection axis.

19. The apparatus of claim 13, wherein in an uncrimped configuration, the wing portion of the second paddle extends to one side of the connection axis.

20. The apparatus of claim 13, wherein in a crimped configuration, the wing portions of the first paddle and the second paddle are configured to be locked in position via the locking mechanism.

21. The apparatus of claim 20, wherein the mating locking pieces cooperatively define a ratchet mechanism.

22. The apparatus of claim 13, wherein the suture apertures in the first paddle and the second paddle each extend along a suture axis perpendicular to the connection axis.

23. The apparatus of claim 22, wherein the ratchet mechanism includes a round portion with one or more teeth positioned on the extension arm and one or more pivoting pawls included on the first paddle within the slot configured to engage the teeth.

24. The apparatus of claim 13, wherein the suture apertures in the first paddle and the second paddle each extend along a suture axis oblique to the connection axis.

25. The apparatus of claim 13, wherein the locking mechanism includes a first mating locking piece on the first paddle and a second mating locking piece on the second paddle.

26. The apparatus of claim 13, further comprising a device including a suture, the suture extending through the suture apertures of the first paddle and the second paddle.

27. The apparatus of claim 13, wherein in an uncrimped configuration, the wing portions of the first paddle and the second paddle extend in substantially the opposite direction from the connection axis.

28. The apparatus of claim 13, wherein in an uncrimped configuration, the wing portions of the first paddle and the second paddle extend in substantially the same direction from the connection axis.

29. The apparatus of claim 13, wherein the first paddle is a base paddle, and the second paddle is a rotating paddle, whereby the second paddle is rotatable with respect to the first paddle.

30. The apparatus of claim 13, wherein in an uncrimped configuration the suture apertures are collinear, and wherein from that uncrimped configuration one of the paddles is capable of rotation through an angle that is greater than 90 degrees.

31. The apparatus of claim 13, wherein in an uncrimped configuration the suture apertures are collinear along a suture axis and the suture axis is not parallel to either wing portion.

32. The apparatus of claim 13, wherein wing portions of the first and second paddles are positioned adjacent each other in an uncrimped configuration.

33. The apparatus of claim 13, wherein wing portions of the first and second paddles are positioned adjacent each other in a crimped configuration.

34. The apparatus of claim 13, wherein the paddles are rotatable with respect to each other around the connection axis.

35. The apparatus of claim 13, wherein the second paddle is rotatable with respect to the first paddle around the connection axis.

* * * * *